United States Patent [19]

Ueno

[11] Patent Number: 4,684,529
[45] Date of Patent: Aug. 4, 1987

[54] PROCESS FOR THE PREPARATION OF IODIZABLE CALCIUM COMPOSITION

[75] Inventor: Toshio Ueno, Higashiyamato, Japan
[73] Assignee: Kabushiki Kaisha Fuji Kikaku, Tokyo, Japan
[21] Appl. No.: 710,200
[22] Filed: Mar. 11, 1985
[30] Foreign Application Priority Data Mar. 9, 1984 [JP] Japan .................................. 59-43813

[51] Int. Cl.[4] .............................................. A23L 3/32
[52] U.S. Cl. ..................................... 426/237; 426/244
[58] Field of Search ........................... 426/237, 244, 1

[56] References Cited

FOREIGN PATENT DOCUMENTS 353286  7/1931  United Kingdom .................... 426/1

Primary Examiner—George Yeung
Attorney, Agent, or Firm—Jordan and Hamburg

[57] ABSTRACT

The present invention relates to a process of the preparation of ionizable calcium composition powder by powdering oyster shells and decomposing the powder. Oyster shells are dried and then powdered. This oyster shell powder is forced from a tubular feeding zone including a screw conveyor into a tubular processing zone, and during the passage through the tubular processing zone the powder is thermally and electrically treated. The processing zone has an electric heater arranged around the passage thereof, and a pair of electrodes arranged on opposite sides of the passages. The oyster shell powder, when it is passed through the processing zone, is heated by the heater and is exposed to an electric discharge by applying a high voltage between the pair of the electrodes, and as a result of this discharge treatment the product powder is highly ionizable.

12 Claims, 2 Drawing Figures

PROCESS FOR THE PREPARATION OF IODIZABLE CALCIUM COMPOSITION

FIELD OF THE INVENTION

The present invention relates to a process for the preparation of an edible ionizable calcium composition using powder of oyster shells as raw materials.

It is to be understood that by "oyster shells" are meant to include species of the genus Ostrea of the Lamellibranchia class. The term "ionized concentration" used herein refers to the value expressed in the unit of microsiemens/centimeter ($\mu$s/cm), and the value can be determined as follows: hydrochloric acid or sodium hydroxide is added to deionized water to prepare an adjusted liquid having a pH of 4.8 and/or an adjusted liquid having a pH of 9.1, 2 g of a sample is added to 100 ml of the adjusted liquid (25° C.), the resulting mixture is stirred for 5 min and after it is allowed to stand for 5 min, the electrical conductivity of the supernatant portion of the mixture is measured.

DESCRIPTION OF THE PRIOR ART

It is known that calcium necessary to the human body can be absorbed more efficiently into the canalis alimentarius as the ionized concentration becomes higher. It is also known that powder of oyster shells are desirable as a source of such calcium. Oyster shells contain well balanced inorganic constituents that are not found in mineral origin calcium, and these inorganic constituents are regarded to act important roles in view of nutrition.

A process for the preparation of ionizable calcium composition powder from oyster shells used as raw material has been practiced, and the process is as follows. FIG. 1 shows a schematic view of an apparatus used in the prior art. The apparatus includes a container 5 illustrated in broken line that contains pairs of equispaced electrodes 1 and 2. The electrodes 1 and 2 are connected respectively via electric wires 7 and 8 with the positive pole and the negative pole of a power source 6. In practice, the spaces between the electrodes 1 and 2 in the container 5 are filled closely with a suitable number of unground oyster shells 3 together with carbon powder 4. Then an electric voltage is applied between the electrodes 1 and 2 so that the unground oyster shells 3 are exposed to the discharge. Thereafter, the oyster shells 3 are taken out of the container 5, the carbon powder adhered to the oyster shells 3 is removed and the oyster shells are reduced to powder in known manner.

The prior method is obviously not good in view of working efficiency and is not suited for mass production. Further, as oyster shells have irregular and fine openings, if the openings are not filled with the carbon powder during the discharge, the heat treatment becomes uniform, and when the obtained oyster shells are reduced to powder, a product high in ionized concentration would not be obtained. When it is tried to acquire a higher ionized concentration, the yield per power consumption becomes low. In addition, the carbon powder adhered to the treated oyster shells is hard to be removed completely, and the residue thereof will be present in the product.

SUMMARY OF THE INVENTION

A general object of the invention is to provide an inexpensive process for the preparation of edible calcium composition powder high in ionized concentration that is useful for the human body in view of nutrition.

A particular object of the invention is to provide a process of mass-producing ionizable calcium composition powder continuously from oyster shells used as raw material.

A further particular object of the invention is to provide a process of modifying a powder of oyster shells under less power consumption into ionizable calcium composition powder that is high in ionized concentration and uniform.

The process for the preparation of ionizable calcium composition powder according to the present invention is distinguished by the fact that after oyster shells are reduced to powder, they are exposed to discharge between a pair of electrodes. A desirable apparatus for carrying out the present process is provided with a tubular feeding zone including a screw conveyor, and a tubular processing zone connected to the feeding zone and containing a passage. The processing zone has an electric heater that surrounds the passage and a pair of electrodes between which the passage is located. Powdered oyster shell is fed by the screw conveyor from the feeding zone to the processing zone through which the powdered oyster shell is forcibly delivered in a compacted manner. During the passage through the processing zone, the oyster shell powder is heated by the electric heater and then exposed to an electric discharge between the electrodes. As a result, it is decomposed as follows:

$$CaCO_3 \rightarrow CaO + CO_2 \uparrow$$

and the calcium oxide formed in the product can be ionized to form calcium bivalent ion via calcium hydroxide when reacted with water.

Though oysters of species of the genus Ostrea of the Lamellibranchia class can be used as raw material, generally preferably species are *Crassostrea gigas* and *Gryphaea nippona* that are known as edible ones. The raw material oyster shells to be reduced to powder are preferably those whose surfaces have been weathered to become smooth and whitened, and for this purpose it is preferable that the raw material oyster shells are weathered previously at a seashore. Prior to powdering, the raw material oyster shells are washed with fresh water, dried, and then mechanically ground by using a known suitable mill. The desirable particle size is less than the size of 80 mesh. Though the heating temperature of the powder at the heater and the voltage applied between the pair of the electrodes would be determined, depending on the ionized concentration of the intended product and the economy including the power consumption, processing period, etc., generally speaking the following ranges would be considered suitable to obtain a product high enough in ionized concentration economically:

The powder feed speed in the tubular processing zone: 20 cm per hour when the inner diameter of the tubular processing zone is 40 mm, The heating temperature of the powder at the heater: 500°–1200° C., desirably 1100° C., The applied voltage: of the order of 6000 V.

According to the present invention, an edible calcium composition powder that is uniform and high in ionized concentration can be mass-produced continuously. According to the present invention, particularly, the present method is advantageous also in that the power consumption per yield is low, that is, compared with the prior art, the power consumption is 1/100 times as low as that of the prior art.

DETAILED DESCRIPTION OF A PREFERRED EMBODIMENT

Figure 1:
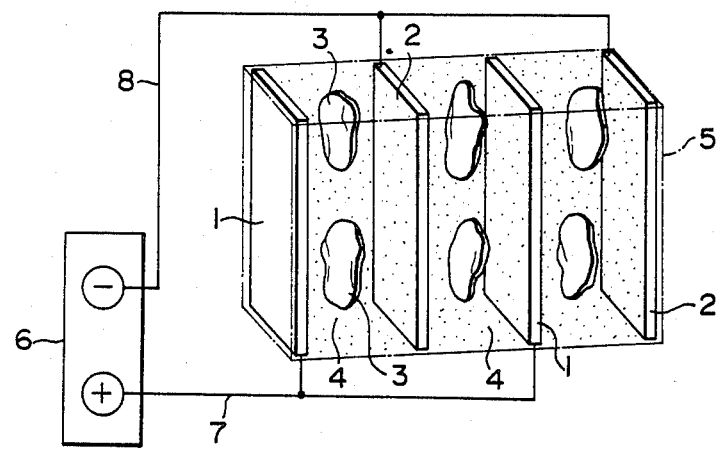
FIG. 1 is an explanatory schematic view of an apparatus used conventionally.
Figure 2:
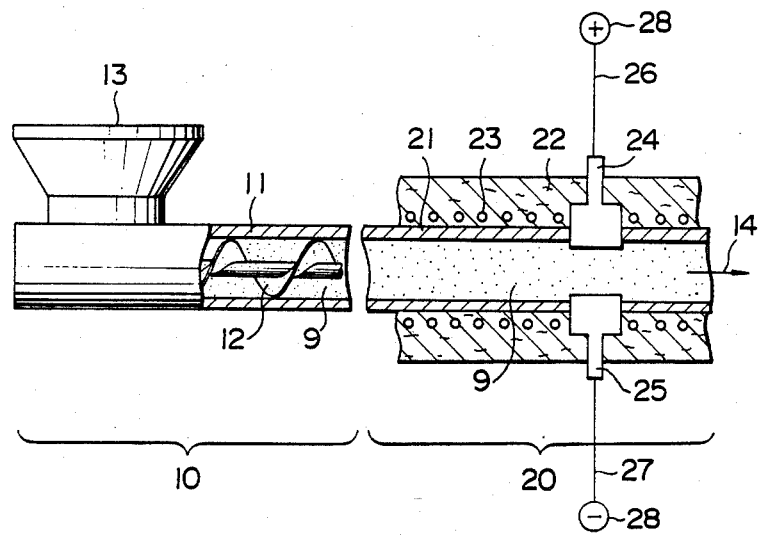
FIG. 2 is a crosssectional view of the essential part of a preferred embodiment of an apparatus for carrying out the present method.

Referring to FIG. 2, an embodiment of a preferred apparatus for carrying out the process for the preparation of ionized calcium according to the invention is illustrated. The apparatus comprises a feeding zone 10 for feeding oyster shell powder 9 and a processing zone 20. The feeding zone 10 comprises a tubular passage member 11 connected with a hopper 13 and having a screw conveyor 20. The screw conveyor 20 is driven by an electric motor (not shown) to be rotated coaxially with the tubular member 11 so that the raw material charged into the tubular member 11 from the hopper 13 is delivered in a direction indicated by an arrow 14. The processing zone 20 comprises a tubular passage member 21 that may actually be located coaxially with the tubular member 11 of the feeding zone 10 and is provided with a heating wire 23 having a heat insulating material 22 wound around the tubular member 21 and a pair of electrodes 24, 25. The electrodes 24, 25 are located at diametrically opposite sides of the tubular member 21, and the electrode surfaces of the electrodes 24, 25 are exposed to the inside of the tubular member 21. Electric wires 26, 27 led from a power source 28 feed an electric power to the respective electrodes 24, 25. The raw material 9 delivered from the feeding zone 10 is forcibly delivered in the passage or cavity defined in the tubular member 21 of the processing zone 20, and during this delivery the raw material 19 is heated by the electric heater 23 and is subjected to the electric current via the pair of the electrodes 24, 25. Thereafter, it is forcibly delivered in the direction indicated in the arrow 14 and reaches an outlet (not shown).

In a preferred embodiment, the following conditions were adopted:

The delivering speed in the processing zone: 20 cm per hour when the inner diameter of the processing zone is 40 mm, The heating temperature of the powder by the heater: 1,100° C., and The voltage applied between the pair of the electrodes: 6,000 V.

Under these conditions, when 3 kg of powder of raw material obtained from oyster shells of *Crassostrea gigas* gathered in Japanese waters were experimentally processed, a calcium composition powder having an ionized concentration of 11,000 μs/cm was obtained, with the period required therefor being 1 hour, and the power consumption being 4 KW×1 hour=4 KWH. For the purpose of comparison, whe the same raw material was processed in a conventional manner to obtain the same yield, the period required therefor was 8 hours and the power consumption was 20 KW×8 hours=160 KWH that correspond to 40 times the former case, and the ionized concentration of the obtained calcium composition powder was 9.236 μs/cm.

While a most preferred embodiment of the present invention has been described in great detail, the present process can also be carried out using, in stead of the tubular member of the continuous processing zone as used in the above embodiment, a batch type container at least one end of which is closed and in which a definite amount of raw material is processed every time.

I claim:

1. A process for the preparation of ionizable calcium composition powder, which comprises the following steps:
   (a) grinding oyster shells to obtain raw material powder,
   (b) continuously and forcibly feeding said raw material powder into a tubular member,
   (c) heating said raw material powder to a temperature from 500° C. to 1,200° C., in said tubular member,
   (d) applying a voltage to said raw material powder heated at said temperature in said tubular member such that decomposition of said raw material powder in said tubular member is substantially accelerated by passing electricity through said raw material powder, and
   (e) continuously removing ionizable calcium composition powder from said tubular member as said heating step and said application of voltage step are continuously applied to said raw material powder.

2. A process according to claim 1, wherein the particle size of said raw material powder is smaller than 80 mesh.

3. A process according to claim 1, wherein said temperature is substantially 1,100° C.

4. A process according to claim 1, wherein said tubular member comprises a tube having an inner diameter of 40 mm, said raw material powder being forcibly moved in said tube at a speed of 20 cm along said tube per hour, and said high voltage applied to said raw material powder is in the order of 6000 V.

5. A process according to claim 2, wherein said temperature is substantially 1,100° C.

6. A process according to claim 2, wherein said tubular member comprises a tube having an inner diameter of 40 mm, said raw material powder being forcibly moved in said tube at a speed of 20 cm along said tube per hour, and said high voltage applied to said raw material is in the order of 6000 V.

7. The product of the process according to claim 1.
8. The product of the process according to claim 2.
9. The product of the process according to claim 3.
10. The product of the process according to claim 4.
11. The product of the process according to claim 5.
12. The product of the process according to claim 6.

* * * * *